United States Patent
Trieu et al.

(10) Patent No.: US 8,353,938 B2
(45) Date of Patent: Jan. 15, 2013

(54) ANNULUS REPAIR SYSTEMS, INSTRUMENTS AND TECHNIQUES

(75) Inventors: Hai H. Trieu, Cordova, TN (US); Lehmann K. Li, Milford, CT (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1408 days.

(21) Appl. No.: 12/001,187

(22) Filed: Dec. 10, 2007

(65) Prior Publication Data

US 2008/0097449 A1 Apr. 24, 2008

Related U.S. Application Data

(62) Division of application No. 10/627,296, filed on Jul. 25, 2003, now Pat. No. 7,326,200.

(51) Int. Cl.
*A61B 17/88* (2006.01)

(52) U.S. Cl. ...................................................... 606/279

(58) Field of Classification Search .................. 606/60, 606/246, 279–281; 623/17.11
See application file for complete search history.

(56) References Cited

U.S. PATENT DOCUMENTS

| | | | |
|---|---|---|---|
| 4,586,496 A | 5/1986 | Keller | |
| 4,586,497 A | 5/1986 | Drapra et al. | |
| 4,697,586 A | 10/1987 | Gazale | |
| 5,549,679 A | 8/1996 | Kuslich | |
| 5,591,235 A | 1/1997 | Kuslich | |
| 5,989,256 A | 11/1999 | Kuslich et al. | |
| 6,093,205 A | 7/2000 | McLeod et al. | |
| 6,126,664 A | 10/2000 | Troxell et al. | |
| 6,156,037 A | 12/2000 | LeHuec et al. | |
| 6,156,067 A * | 12/2000 | Bryan et al. | 623/17.15 |
| 6,206,922 B1 * | 3/2001 | Zdeblick et al. | 623/17.11 |
| 6,261,295 B1 | 7/2001 | Nicholson et al. | |
| 6,264,655 B1 * | 7/2001 | Pisharodi | 606/247 |
| RE37,479 E | 12/2001 | Kuslich | |
| 6,371,986 B1 | 4/2002 | Bagby | |
| 6,371,990 B1 | 4/2002 | Ferree | |
| 6,432,106 B1 * | 8/2002 | Fraser | 623/17.11 |
| 6,432,107 B1 * | 8/2002 | Ferree | 606/247 |
| 6,471,724 B2 * | 10/2002 | Zdeblick et al. | 623/17.16 |
| 6,576,017 B2 * | 6/2003 | Foley et al. | 623/17.16 |
| 2002/0120270 A1 | 8/2002 | Trieu et al. | |
| 2002/0151893 A1 | 10/2002 | Santilli | |
| 2003/0195514 A1 | 10/2003 | Trieu et al. | |
| 2004/0010254 A1 | 1/2004 | Cook et al. | |
| 2004/0039392 A1 | 2/2004 | Trieu | |
| 2006/0074425 A1 | 4/2006 | Suttlerin et al. | |

FOREIGN PATENT DOCUMENTS

| | | |
|---|---|---|
| WO | WO 01/10316 | 2/2001 |
| WO | WO 01/28464 | 4/2001 |
| WO | WO 02/058599 | 8/2002 |
| WO | WO 02/067793 | 9/2002 |
| WO | WO 03/011155 | 2/2003 |

* cited by examiner

*Primary Examiner* — Kevin T Truong
*Assistant Examiner* — Michael Araj

(57) ABSTRACT

Systems and methods for repairing annulus defects include at least one blocking member positionable in or adjacent to the annulus defect, and at least one anchor for securing the blocking member to adjacent tissue recessed into the adjacent vertebrae. The blocking member extends at least partially across the annulus defect for repair of the defect and/or retention of nucleus material, one or more implants, bio-compatible materials or device, and/or other objects positioned in the disc space. Instruments are provided to facilitate preparation of the implantation site of the annulus repair system.

10 Claims, 7 Drawing Sheets

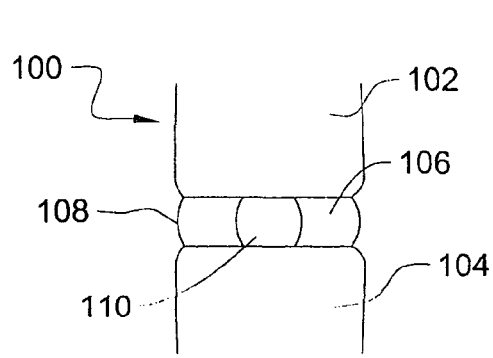
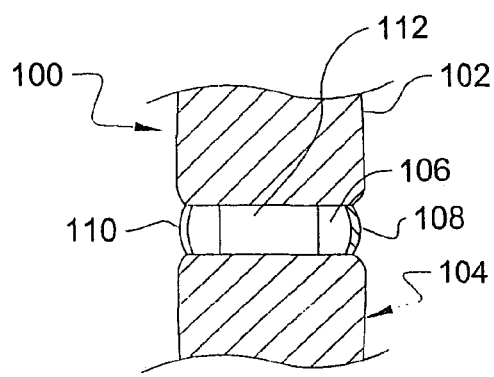
Fig. 3          Fig. 4
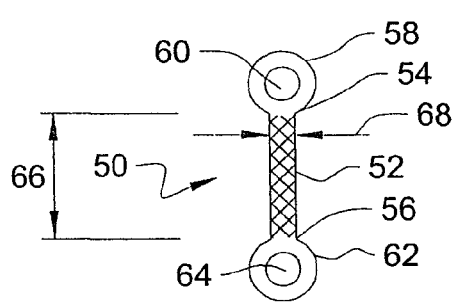
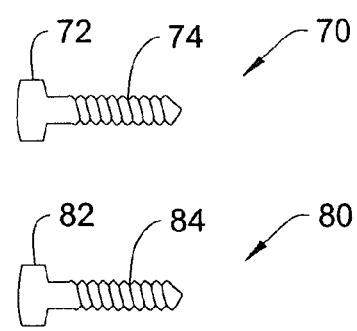
Fig. 1          Fig. 2
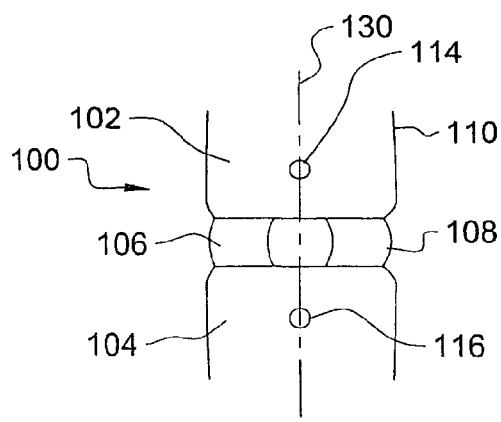
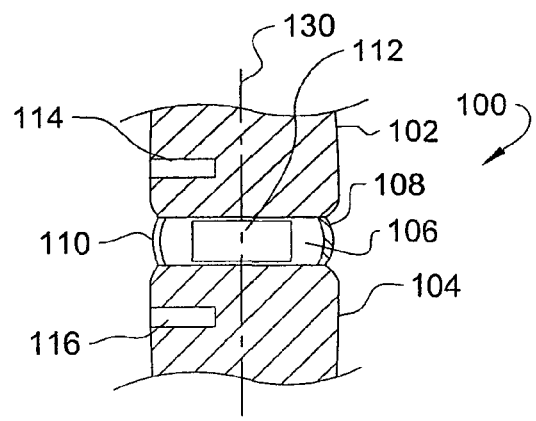
Fig. 5          Fig. 6

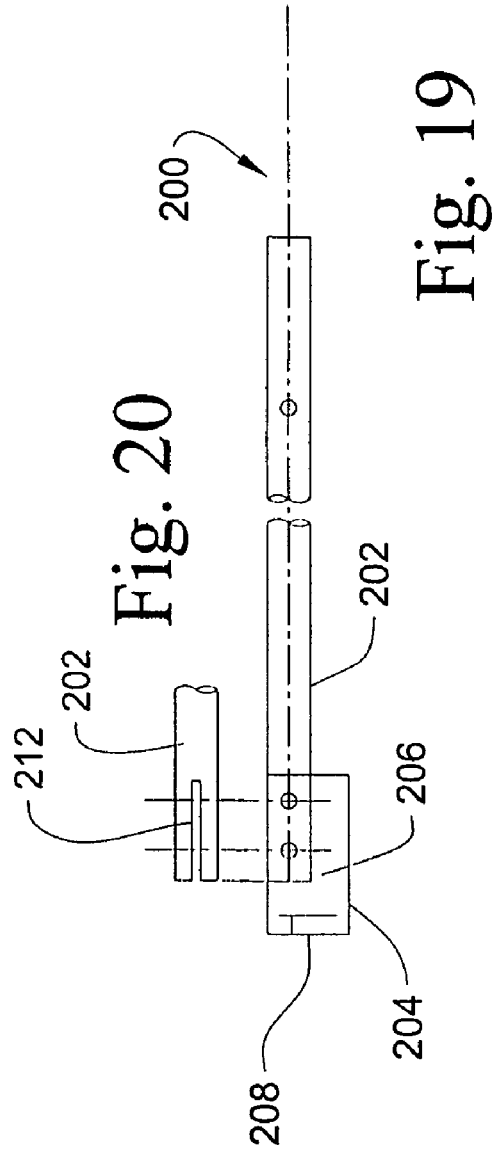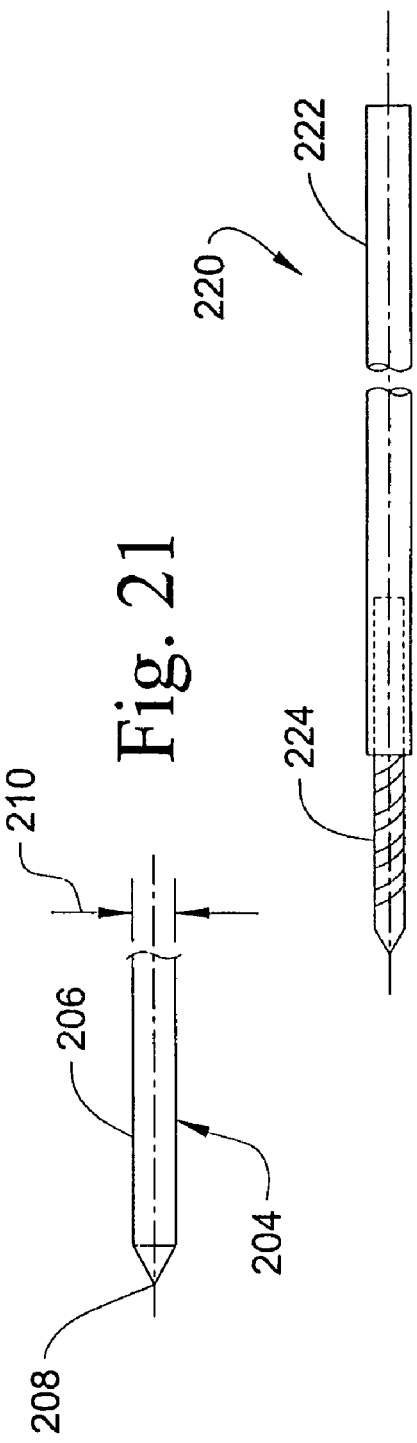

ANNULUS REPAIR SYSTEMS, INSTRUMENTS AND TECHNIQUES

CROSS-REFERENCE TO RELATED APPLICATION

This application is a divisional of U.S. patent application Ser. No. 10/627,296 filed on Jul. 25, 2003 now U.S. Pat. No. 7,326,200, which is incorporated herein by reference in its entirety.

BACKGROUND

The present invention relates generally to the field of spinal surgery, and more particularly to systems and techniques for repairing an annulus defect.

There are various surgical procedures and conditions that create a defect in the annulus fibrosis, such as, for example, an annulotomy, a discectomy, nucleotomy, implantation of artificial disc nucleus or artificial disc prosthesis, repair of a disc herniation, and annulus degeneration. Repair of annulus defects is normally perceived as time consuming and ineffective. Thus, annulus defects are commonly left unrepaired. This may lead to a higher incidence of disc herniation or reherniation, or expulsion of the implant from the disc space.

In those procedures where the annulus is repaired via sutures that attempt to close the defect by pulling the surrounding tissue together, there are difficult challenges encountered. Often, the annulus defect is a relatively large hole that is difficult to close with conventional suturing techniques. It can also be difficult to actively engage the sutures in the surrounding annulus tissues, and the sutures could cut or tear through the annulus tissues after the repair has been made.

SUMMARY

The present invention is directed to systems, devices, techniques and methods for repairing annulus defects. Embodiments of the systems and devices include at least one blocking member positionable in or adjacent to the annulus defect and attachable to adjacent tissue. Instruments for preparing the vertebrae for attachment of the blocking member in and/or adjacent to the annulus defect are also provided. The blocking member extends at least partially across the annulus defect for repair of the defect and/or retention of nucleus material, one or more implants, bio-compatible materials or devices, and/or other objects positioned in the disc space.

BRIEF DESCRIPTION OF THE DRAWINGS

FIG. 1 is an elevation view of one embodiment annulus repair device.

FIG. 2 is an elevation view of one embodiment pair of fasteners for securing the device of FIG. 1 to adjacent vertebrae.

FIG. 3 is an elevation view of a spinal column segment with an annulus defect.

FIG. 4 is a sectional view through the defect of the spinal column segment of FIG. 3.

FIG. 5 is an elevation view of the spinal column segment with holes formed in the adjacent vertebrae.

FIG. 6 is a sectional view through the defect of the spinal column segment of FIG. 5.

FIG. 19 is an elevation view of one embodiment cutting instrument.

FIG. 20 is a plan view of a distal portion of the shaft of the instrument of FIG. 19.

FIG. 21 is a plan view of a distal portion of a cutting blade comprising a portion of the instrument of FIG. 19.

FIG. 22 is an elevation view of a drilling instrument.

DESCRIPTION OF THE ILLUSTRATED EMBODIMENTS

Figure 7:
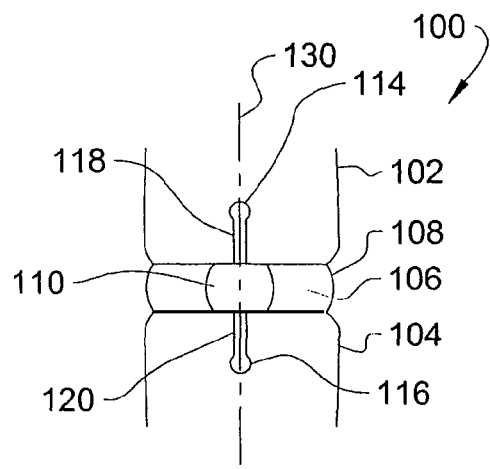
FIG. 7 is an elevation view of the spinal column segment with recesses formed in the adjacent vertebrae in communication with the holes.

For the purposes of promoting an understanding of the principles of the invention, reference will now be made to embodiments illustrated in the drawings and specific language will be used to describe the same. It will nevertheless be understood that no limitation of the scope of the invention is thereby intended. Any such alterations and further modifications in the illustrated embodiments, and any such further applications of the principles of the invention as illustrated herein are contemplated as would normally occur to one skilled in the art to which the invention relates.

The annulus repair system and methods include a blocking member retained within or adjacent a defect in the annulus fibrosis of a spinal disc. The blocking member can block all or a portion of the defect or void within the annulus fibrosis, such as may be caused by surgery or disc herniation. The blocking member is retrained in a substantially fixed position within the defect or void relative to adjacent soft or hard tissue. The blocking member can include one or more attachment portions connectable to or integrally formed with the blocking member. The attachment portions may be engaged to bone or other tissue adjacent to the defect or void.

With respect to the various embodiments described herein, the blocking member is recessed in or positioned within the defect so that it extends substantially across the annulus defect. The recessed positioning of the blocking member facilitates placement of the blocking member toward the inner wall of the annulus, and thus adjacent the nucleus and/or implant positioned in the disc space. The blocking member resists implant and/or nucleus migration into the annulus defect, providing an effective blocking mechanism and repair of the annulus defect.

The attachment portions and/or anchors associated with the blocking member can be recessed within the adjacent bone portions to facilitate attachment of the blocking member in a position within the annulus defect. Anchor can directly attach the blocking member to adjacent tissue. If provided, the attachment portions can be joined or fixed to the blocking member using various devices and/or techniques, or can be integrally formed with or be an extension of the blocking member. The blocking member can be joined or attached to the attachment portion by, for example, sewing the attachment portion to the blocking member, thermal welding or bonding, adhesive bonding, three dimensional weaving or braiding, screws, staples, pins, tacks, crimps, or rivet fixation, for example. Furthermore, the attachment portion can be secured to the blocking member either before or after the blocking member is placed within the annulus defect. It is further contemplated that the attachment portions can be provided in the form of sutures, threads, cables, or wires, for example, that engage the blocking member and secure the blocking member to anchors engaged to tissue adjacent the defect.

The blocking member can be provided in various forms. Examples include a blocking member that comprises a suture, tether, mesh, sheet, plug, scaffold or combinations thereof. The blocking member can be fabricated from components that are flexible or exhibit at least some flexibility. Examples of such components include woven fabric tubing, woven and non-woven mesh, or braided or woven structures, folded woven fabric, tethers, cords, planar members, bands, wires, cables, or any other component capable of extending across an annulus defect. Additionally, the blocking member may be resilient and/or elastic so it can assume various shapes during and after insertion and attachment. Growth factors or cells can be incorporated into the blocking member to accelerate the annulus repair process. Growth factors can be transforming growth factor β1, insulin-like growth factor 1, platelet-derived growth factor, fibroblast growth factor, bone morphogenetic protein (BMP), LIM mineralization protein (LMP) and combinations thereof.

The blocking member can be made from any biocompatible material, material of synthetic or natural origin, and material of a resorbable or non-resorbable nature. Examples of suitable blocking member material include autograft, allograft or xenograft; tissue materials including soft tissues, connective tissues, demineralized bone matrix and combinations thereof; resorbable materials including polylactide, polyglycolide, tyrosine-derived polycarbonate, polyanhydride, polyorthoester, polyphosphazene, calcium phosphate, hydroxyapatite, bioactive glass, collagen, albumin, fibrinogen and combinations thereof; and non-resorbable materials including polyethylene, polyester, polyvinyl alcohol, polyacrylonitrile, polyamide, polytetrafluorethylene, poly-paraphenylene terephthalamide, cellulose, and combinations thereof.

The anchors can be made from any biocompatible material, including synthetic or natural autograft, allograft or xenograft tissues, and can be resorbable or non-resorbable nature. Examples of tissue materials include hard tissues, connective tissues, demineralized bone matrix and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials include high performance polymers, such as polyetheretherketone, carbon-reinforced polymer composites, shape-memory alloys, titanium, titanium alloys, cobalt chrome alloys, stainless steel, and combinations thereof.

The anchors can be solid, porous, semi-porous, fenestrated, cannulated, and combinations thereof to provide strength and bone ingrowth when desired. The outer surfaces of the anchors can be smooth, roughened, porous, serrated, or combinations thereof to provide the desired pullout resistance. The anchors can be provided with one or more movable components that resist anchor pullout, such as wings, gulls or flexible barbs. It is further contemplated that the anchors can be configured for positioning into and engagement with the tissue by any one or combination of rotation force, impaction force, inserted into an opening and thereafter expanded to engage the surrounding tissue, adhesion or bonding, fusion, and tissue ingrowth, for example. The anchors can be provided in various forms, including screws, tacks, pins, staples, suture anchors, and wedges, for example.

Referring to FIGS. 1 and 2 there is illustrated annulus repair system according to one embodiment. The annulus repair system includes a blocking member 50 and a pair of anchors 70, 80 to secure blocking member 50 to tissue in the patient. Blocking member 50 includes a body 52 extending between a first end 54 and an opposite second end 56. Blocking member 50 includes a length between first end 54 and second end 56 sufficient to span the annulus defect between the tissue structure to which blocking member 50 is to be attached. Body 52 includes a width 68 sufficient to extend across at least a portion of the annulus defect to provide an effective mechanical barrier. In one embodiment, width 68 extends across at least 10% of the width of the annulus defect. In another embodiment, width 68 extends across at least 50% of the annulus defect. In another embodiment, body 52 is provided with a width 68 in the range from about 10% to about 50%. of the width of the annulus defect. In a further embodiment, width 68 extends across substantially the entire width of the annulus defect. In still another embodiment, body 52 includes a width 68 that is greater than the width of the annulus defect, and body 52 is compressed laterally to fit within the annulus defect.

First end 54 includes an attachment portion 58 with a passage 60 therethrough to receive anchor 70. Second end 56 includes an attachment portion 62 with a passage 64 therethrough to receive anchor 80. Anchor 70 can be provided with a proximal portion 72 and a distal engagement portion 74. Similarly, anchor 80 can be provided with a proximal portion 82 and a distal engagement portion 84. Anchors 70, 80 are illustrated in the form of bone screws with enlarged heads at proximal portions 72, 82 and threaded distal engagement portions 74, 84. Proximal portions 72, 82 each include a head that abuts against the respective attachment portion 58, 62 when positioned through the corresponding passage 60, 64 to secure blocking member 50 to the tissue structure to which anchors 70, 80 are engaged.

In one specific embodiment, attachment portions are in the form of circular eyelets made from a suitable bio-compatible metal or polymeric material, and provide a rigid body against which the proximal portions 72, 82 of anchors 70, 80 abut. In one form, the attachment portions can be provided with a spherically shaped seat centered about a circular passage 60, 64 for abutment with spherically shaped surfaces of the heads of anchors 70, 80, permitting multi-axial angular orientations of anchors 70, 80 relative to attachment portions 58, 62. In another form, attachment portions 58, 62 are configured to engage anchors 70, 80 to provide a fixed orientation of anchors 70, 80 therethrough. It is further contemplated that one attachment portion 58, 62 and its corresponding anchor 70, 80 provide variable angle anchor placement, and the other attachment portion 58, 62 and anchor 70, 80 permit fixed angle anchor placement.

Anchors 70, 80 can include a tool engagement opening in the proximal end of proximal portions 72, 82 to facilitate application of a rotational driving force, such as is provided with screw driver. Other embodiments contemplate other forms for anchors 70, 80 as discussed above, including anchors that are driven into the bony tissue with impaction forces or linear advancement. It is also contemplated that anchors 70, 80 could be provided integrally with the respective attachment portions 58, 62. In a further form, it is contemplated that attachment portions 58, 62 are provided without a passage, and anchors 70, 80 penetrate attachment portions 58, 62. In still a further form, anchors 70, 80 penetrate body 52 to engage blocking member 50 to the adjacent tissue.

Referring now further to FIGS. 3 and 4, there is shown a spinal column segment 100 including a first vertebra 102, a second vertebra 104, and a spinal disc space 106 therebetween. Spinal disc space 106 includes annulus 108 extending therearound. Annulus 108 includes a defect 110 formed therein. Defect 110 can be created or formed for any one or combination of reasons, including an annulotomy, a discectomy, nucleotomy, implantation of artificial disc nucleus or artificial disc prosthesis, repair of a disc herniation, or rip, tear or other degeneration or condition associated with the annulus. It is contemplated that the annulus repair systems can be positioned in a defect at any location about vertebrae 102, 104, including the anterior, antero-lateral, oblique, lateral, posterior-lateral or posterior portions of vertebrae 102, 104.

It is contemplated that an implant 112 can be positioned in spinal disc space 106 between vertebrae 102, 104 through defect 110. Implant 112 can be one or more interbody spacers, fusion implants, artificial discs, artificial nucleus, or any other device suitable for placement between vertebrae. It is further contemplated that implant 112 not be provided in spinal disc space 106.

Figure 8:
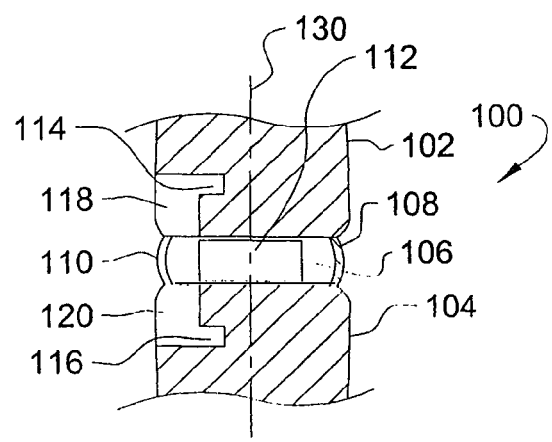
FIG. 8 is a sectional view through the defect of the spinal column segment of FIG. 7.

In FIGS. 5 and 6, hole 114 is formed in vertebra 102, and hole 116 is formed in vertebra 104. Holes 114, 116 are aligned across defect 110. In the illustrated embodiment, holes 114, 116 are spaced from the endplate of the respective vertebra 102, 104 so that blocking member 50 can extend along the entire height of the defect between vertebrae 102, 104. In FIGS. 7 and 8, recess 118 is formed in vertebra 102 and extends from the endplate of vertebra 102 to hole 114. Recess 120 is formed in vertebra 104 and extends between the endplate of vertebra 104 and hole 116. Recesses 118, 120 communicate with defect 110, and extend in the general direction of central axis 130 of the spinal column to receive blocking member 50 in a corresponding orientation. It is further contemplated that recesses 118, 120 can extend transversely to central axis 130 with recesses 118, 120 communicating with holes 114, 116 and defect 110.

Figure 9:
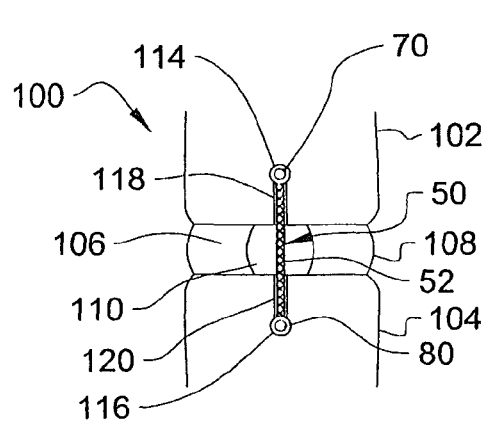
FIG. 9 is an elevation view of the spinal column segment with the repair device of FIG. 1 secured in the holes and recesses formed in the adjacent vertebrae.
Figure 10:
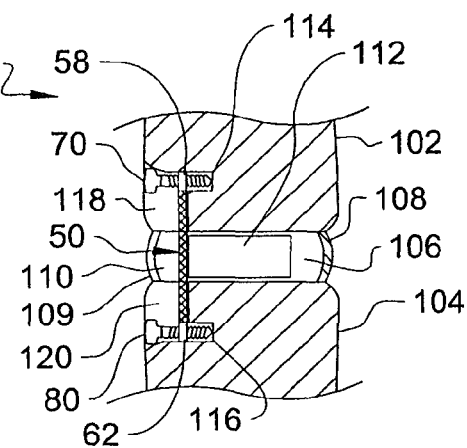
FIG. 10 is a sectional view through the defect of the spinal column segment of FIG. 9.

In FIGS. 9 and 10, blocking member 50 is positioned with body 52 in defect 110 and in recesses 118, 120. Attachment portion 58 is positioned in hole 114, and attachment portion 62 is positioned in hole 116. Anchor 70 extends through attachment portion 58, and secures blocking member 50 in hole 114 and recess 118. Anchor 80 extends through attachment portion 62, and secures blocking member 50 in hole 116 and recess 120.

In the secured position, body 52 of blocking member 50 is offset from an outer surface 109 of annulus 108 toward disc space 106. This permits blocking member 50 to block implant 112 and/or nucleus material in disc space 106 before it exits defect 110. The recessed blocking member 50 further facilitates attachment of an exterior stabilization device, such as a spinal plate, along the outer surface 109 of annulus 108 and the outer surfaces of vertebrae 102, 104 without interference from blocking member 50 or anchors 70, 80. In addition, blocking member 50 provides an effective mechanical barrier, while annulus tissue at defect 110 is permitted to grow and/or repair without being subject to stresses that might result from the implant and/or nucleus material attempting to expel through defect 110. Blocking member 50 can also restrain motion of the spinal column segment by limiting separation of vertebrae 102, 104.

Figure 11:
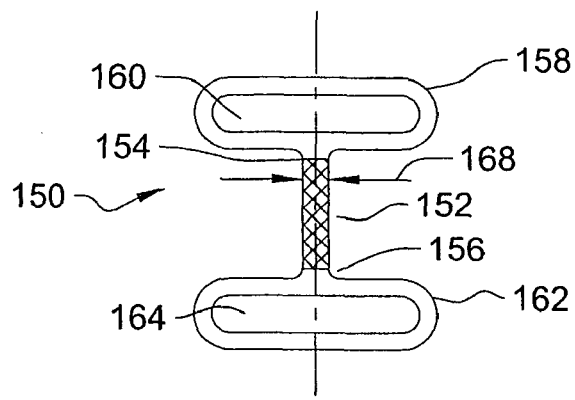
FIG. 11 is an elevation view of another embodiment annulus repair device.
Figure 12:
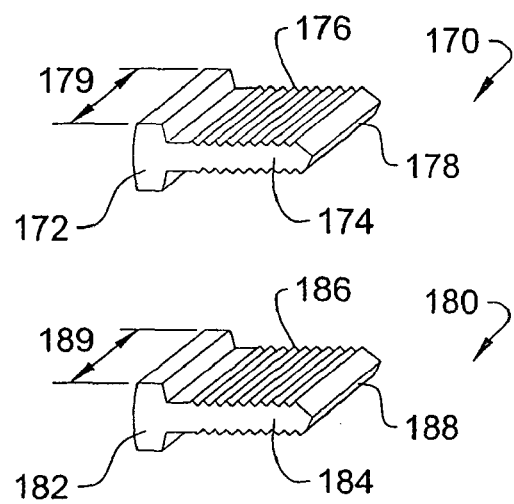
FIG. 12 is an elevation view of one embodiment pair of fasteners for securing the device of FIG. 11 to adjacent vertebrae.

Referring to FIGS. 11 and 12 there is illustrated another embodiment annulus repair system. The annulus repair system includes a blocking member 150 and a pair of anchors 170, 180 to secure blocking member 150 to tissue in the patient. Blocking member 150 includes a body 152 extending between a first end 154 and an opposite second end 156. Blocking member 150 includes a length between first end 154 and second end 156 sufficient to span the annulus defect between the tissue structure to which blocking member 150 is to be attached. Body 152 includes a width 168 sufficient to extend across at least a portion of the annulus defect to provide an effective mechanical barrier as discussed above with respect to blocking member 50.

First end 154 includes an attachment portion 158 with a passage 160 therethrough to receive anchor 170. Second end 156 includes an attachment portion 162 with a passage 164 therethrough to receive anchor 180. Anchor 170 can be provided with a proximal portion 172 and a distal engagement portion 174. Similarly, anchor 180 can be provided with a proximal portion 182 and a distal engagement portion 184. Proximal portions 172, 182 each include an enlarged head that abuts against the respective attachment portion 158, 162 when positioned through the corresponding passage 160, 164 to secure blocking member 150 to the tissue structure to which anchors 170, 180 are engaged.

Anchors 170, 180 are illustrated in the form of bone interference devices with elongated with engaging surfaces 176, 186 formed along distal engagement portions 174, 184. Anchor 170 includes a width 179, and anchor 180 includes a width 189. Widths 179, 189 provide a surface area along and across engagement portions 174, 184 for engagement with the adjacent tissue. Engaging surfaces 176, 186 include ridges and valley between adjacent ridges that extend transversely to the insertion direction of anchors 170, 180. A pointed distal end 178, 188 facilitates penetration of anchor 170, 180 into bony tissue. Anchors 170, 180 can be inserted by applying an impact force to proximal portions 172, 182 that drives engagement portions 174, 184 into the bony tissue.

In one specific embodiment, attachment portions 158, 162 are in the form of oval-shaped or elongated eyelets made from a suitable bio-compatible metal or polymeric material, and provide a rigid body against which the proximal portions 172, 182 of anchors 170, 180 abut. Other embodiments contemplate other forms for anchors 170, 180 as discussed above. It is also contemplated that multiple anchors could be positioned along the width of passage 160, 164. In a further form, it is contemplated that attachment portions 158, 162 are provided without a passage, and anchors 170, 180 penetrate attachment portions 158, 162 or body 152 of blocking member 150.

Widths 179, 189 of anchors 170, 180 can be greater than width 168 of body 152 of blocking member 150. In one specific embodiment, widths 179, 189 are each at least twice as great as width 168, providing anchors 170, 180 with greater surface area to engage the adjacent bony tissue and resist pullout forces that may be applied to blocking member 50. Other embodiments contemplate widths 179, 189 for anchors 170, 180 that are less than twice the width 168 of blocking member 150, or less than width 168 of blocking member 152.

Figure 13:
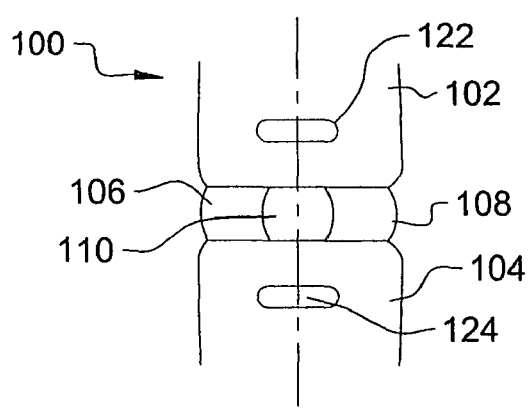
FIG. 13 is an elevation view of the spinal column segment with holes formed in the adjacent vertebrae.
Figure 14:
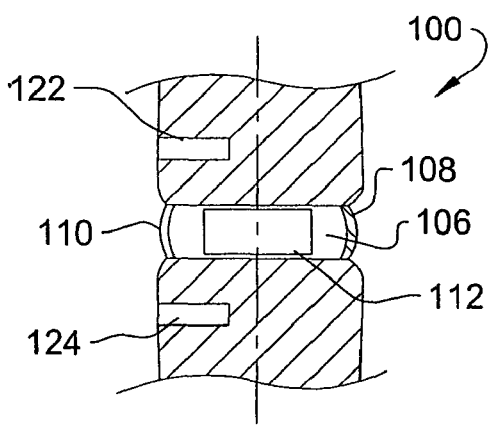
FIG. 14 is a sectional view through the defect of the spinal column segment of FIG. 13.

In FIGS. 13 and 14, hole 122 is formed in vertebra 102, and hole 124 is formed in vertebra 104. Holes 122, 124 are aligned with defect 110. In the illustrated embodiment, holes 122, 124 are spaced from the endplate of the respective vertebra 102, 104 so that blocking member 150 can extend along defect 110 between vertebrae 102, 104. Holes 122, 124 are elongated and extend transversely to the central axis 130 of the spinal column axis to receive anchors 170, 180 in corresponding orientation relative to central axis 130. Holes 122, 124 are each provided with a width sized to accommodate the attachment portion 158, 162 and anchor 170, 180 to be positioned therein.

Figure 15:
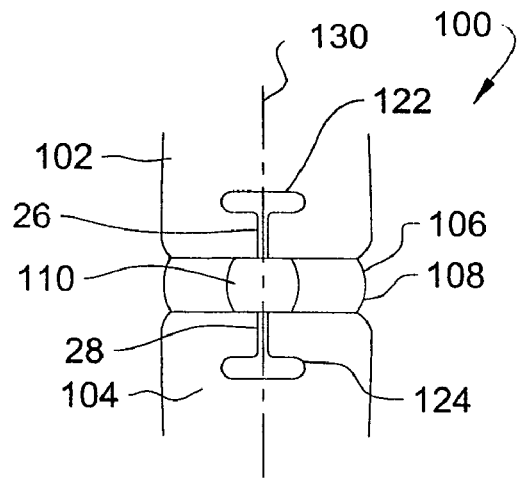
FIG. 15 is an elevation view of the spinal column segment with recesses formed in the adjacent vertebrae in communication with the holes.
Figure 16:
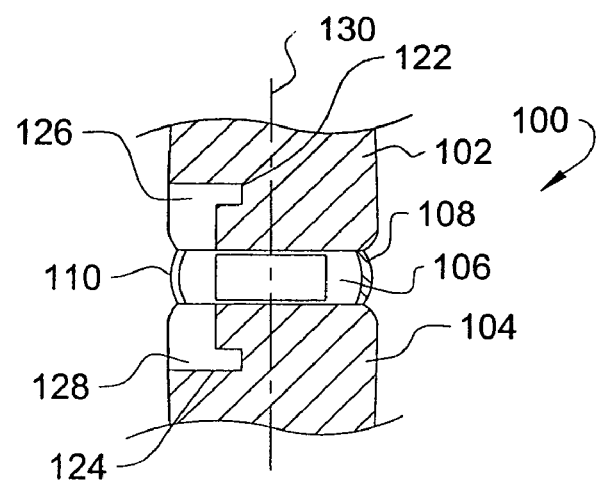
FIG. 16 is a sectional view through the defect of the spinal column segment of FIG. 15.

In FIGS. 15 and 16, recess 126 is formed in vertebra 102 and extends from the endplate of vertebra 102 to hole 122. Recess 128 is formed in vertebra 104 and extends between the endplate of vertebra 104 and hole 124. Recesses 126, 128 provide communication for holes 124, 126 with defect 110.

Figure 17:
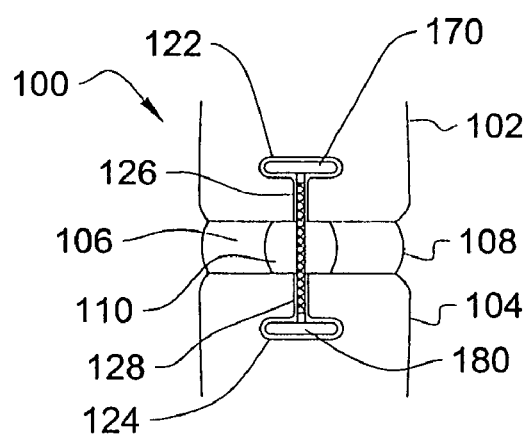
FIG. 17 is an elevation view of the spinal column segment with the repair device of FIG. 11 secured in the holes and recesses formed in the adjacent vertebrae.
Figure 18:
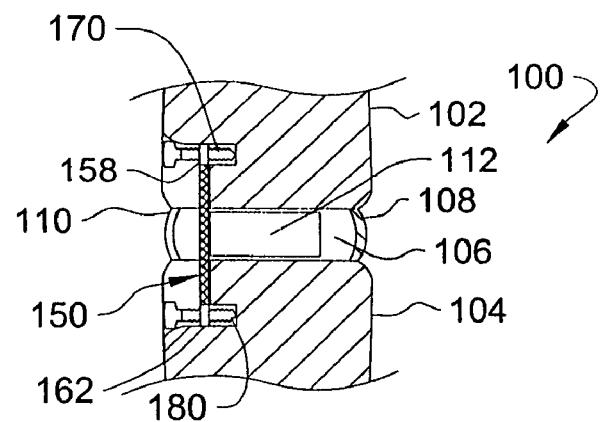
FIG. 18 is a sectional view through the defect of the spinal column segment of FIG. 17.

In FIGS. 16 and 17, blocking member 150 is positioned with body 152 in defect 110 and in recesses 126, 128. Attachment portion 158 is positioned in hole 122, and attachment portion 162 is positioned in hole 124. Anchor 170 extends through attachment portion 158, and secures blocking member 150 in hole 122 and recess 126. Anchor 180 extends through attachment portion 162, and secures blocking member 150 in hole 124 and recess 128.

Referring to FIGS. 19-21, there is shown one embodiment instrument for forming recesses 118, 120 or recesses 126, 128 in the vertebrae 102, 104. Cutting instrument 200 includes an elongated shaft 202 and a cutting blade 204 at a distal end of shaft 202. Blade 204 includes a body 206 that includes a distal cutting end 208. Body 206 includes a width 210 that corresponds to the width of the recess to be formed. Cutting end 208 includes a sharp edge to facilitate penetration into bony tissue, and is tapered distally from a width 210 to facilitate formation of the recess. Shaft 202 includes a distally opening slot 212 to receive a proximal portion of body 206 therein for attachment thereto. Blade 204 projects distally from the distal end of shaft 202 a sufficient distance to form a recess of desired depth into the vertebra. Blade 204 further projects along one side of shaft 202 to facilitate formation of a recess in the vertebra that includes a desired length along the central axis of the spinal column.

FIG. 22 shows one embodiment of an instrument for forming holes 114, 116 in the vertebrae. Drill 220 includes a shaft 222 and a distal cutting tip 224 in the form of a drill bit. Cutting tip 224 can form circular holes in the vertebra upon application of a rotary force thereto. Holes 122, 124 can be formed by drilling a plurality of overlapping holes with drill 220, or by moving drill 220 laterally along a suitable guide. Other bone cutting or removal instruments are also contemplated for forming recesses 118, 120, 126, 128 and/or holes 114, 116, 122, 124, including burrs, mills, chisels, and scrapers, for example.

Figure 23:
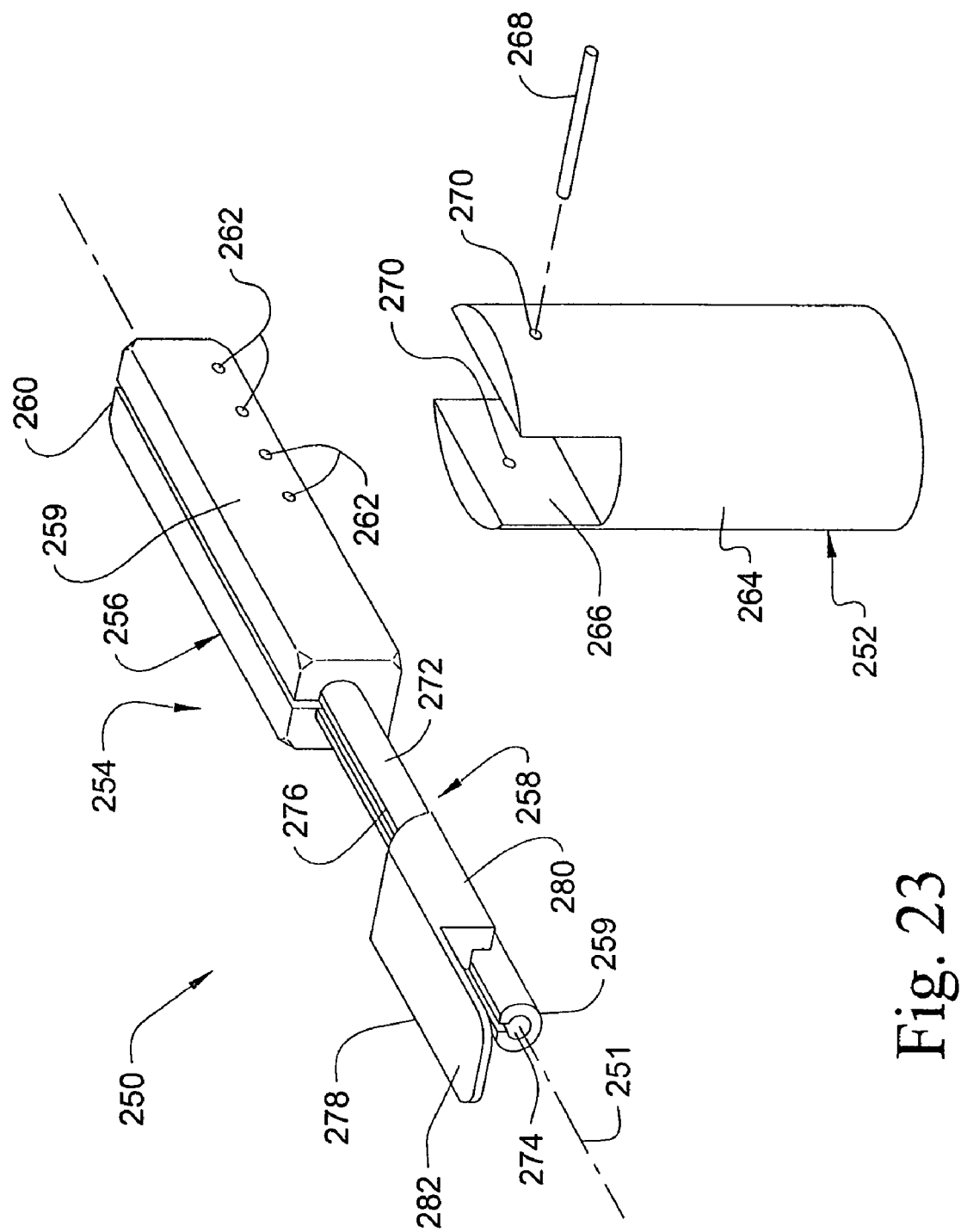
FIG. 23 is a perspective view on one embodiment guide instrument usable with the cutting instrument and drilling instruments of FIGS. 19 and 22.
Figure 24:
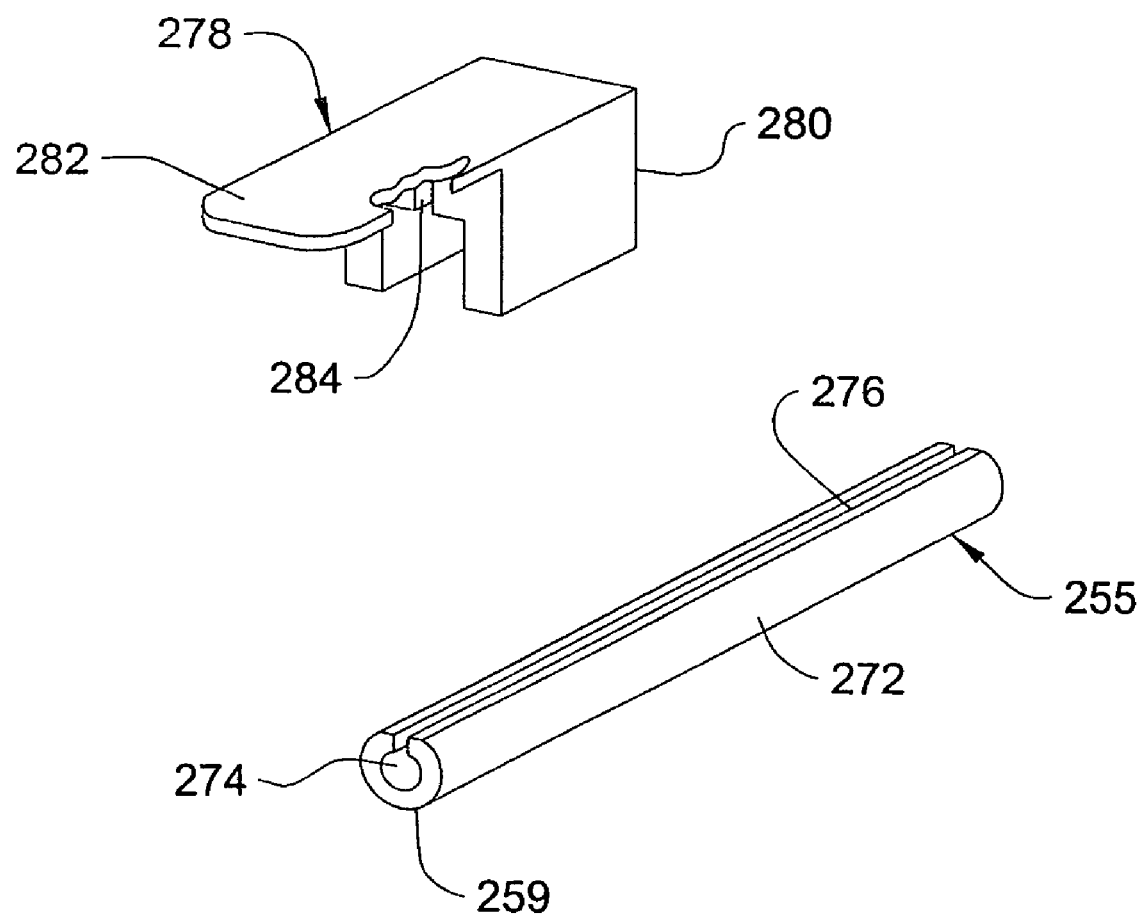
FIG. 24 is an exploded perspective view of a distal portion of the guide instrument of FIG. 23.

FIGS. 23 and 24 provide an example of a guide instrument 250 that can be used in the formation of, for example, hole 114 and the recess 118 in communication therewith in vertebrae 102, or hole 116 and recess 120 in vertebra 104. It is still further contemplated that guide 250 can be adapted to guide formation of holes 122, 124 and recesses 126, 128 in communication therewith. Guide instrument 250 can be used to guide drill 220 and cutting instrument 200 to the proper locations on vertebrae 102, 104 relative to defect 110.

In the illustrated embodiment, guide instrument 250 includes a handle assembly 252 attachable to a guide assembly 254. Guide assembly 254 extends along longitudinal axis 251 and includes a proximal portion 256 and a distal portion 258. Distal portion 258 is positionable inside the patient, with at least a portion of proximal portion 256 accessible by the surgeon. Proximal portion 256 includes a shaft 259 having a number of engagement holes 262 formed therein. Handle assembly 252 include a handle member 264 with a slotted end 266 adapted to receive shaft 259. An engaging member 268 in the form of a pin or the like is positionable through passages 270 of handle member 264 for engagement with an aligned engagement hole 262 extending through shaft 259. The number of engagement holes 262 provide to the surgeon the ability to adjust the length of guide instrument 250 extending distally from handle assembly 252.

Distal portion 258 includes an elongated guide member 272 extending along longitudinal axis 251 of guide instrument 250. Guide member 272 includes a passage 274 extending therethrough along longitudinal axis 251. A slot 276 extends through a wall of guide member 272 and is in communication with passage 274. Passage 274 and slot 276 open at distal end 259 of distal portion 258. Passage 274 and slot 276 further extend along shaft 259 of proximal portion 256 to receive instruments therethrough from proximal end 260 of shaft 259.

Distal portion 258 further includes a positioning member 278 along a distal portion of guide member 272. Positioning member 278 includes a body portion 280 secured to guide member 272. Body portion 280 includes a slot 284 therethrough aligned with slot 276 of guide member 272. A positioning flange 282 extends distally from body portion 280, and projects distally beyond distal end 259. Positioning flange 282 is sized for positioning in the annulus defect in contact with adjacent vertebral plate with distal end 259 of guide member 272 in contact with or adjacent to vertebra 102, 104 in which it is desired to form a hole and recess.

It is contemplated that passage 274 can be circular to guide placement of a drill bit for forming a circular hole, such as holes 114, 116. It is further contemplated that passage 274 can be oval in shape to guide formation of elongated holes, such as discussed above with respect to holes 122, 124. It is further contemplated that guide member can be provided with a reduced cross-sectional size to facilitate positioning through a minimally invasive access portal, such as a sleeve, cannula, split-tube retractor, a retractor blade, or micro-incision, for example.

In use, distal portion 258 is positioned through an incision, tube or other access portal to the annulus defect. Positioning flange 282 of positioning member 278 is placed into the annulus defect and in contact with the vertebral endplate of a vertebra in which it is desired to form a hole and recess. A drilling instrument, such as drill 220, is guided to the vertebra through passage 274 of guide member 272 to form a hole in the vertebra. After formation of the hole, the drilling instrument is removed, and a cutting instrument, such as cutting instrument 200, is guided through passage 274 with its blade projecting through slot 276 while shaft 202 if cutting instrument 200 is guided in passage 274. The cutting blade is advanced into the vertebral body to form the recess in communication with and extending between the formed hole and the defect. Guide instrument 250 is then removed, and a hole and recess are formed in the other vertebral body in communication with the annulus defect.

The guide instrument is then removed, and an annulus repair system is positioned in the prepared recesses and holes and secured thereto with anchors. The bony tissue along the sides of the recesses laterally restrains the blocking member to resist it moving laterally relative to the defect, which could enlarge the unblocked portion of the defect. Anchors engaged to ends of the blocking member provide axial constraint for the blocking member, and maintain the blocking member in the recesses.

While embodiments of the invention have been illustrated and described in detail in the drawings and foregoing description, the same is to be considered as illustrative and not restrictive in character, it being understood that all changes and modifications that come within the spirit of the invention are desired to be protected.

What is claimed is:

1. A method for repairing an annulus defect of a spinal disc, comprising:
    forming a recess in a first vertebra on at least one side of the spinal disc in communication with the defect, wherein forming the recess includes placing a distal portion of a guide member in the defect in contact with an endplate of the first vertebra and guiding a cutting instrument with the guide member to form the recess from the endplate into the first vertebra along the central axis of the spinal column;
    forming a recess in a second vertebra on at least one side of the spinal disc in communication with the defect, wherein forming the recess includes placing the distal portion of the guide member in the defect in contact with an endplate of a second vertebra on the other side of the spinal disc and guiding the cutting instrument with the guide member to form a second recess from the endplate of the second vertebra along the central axis of the spinal column;
    positioning a blocking member in the defect and into the recess;
    engaging the blocking member to the vertebra;
    guiding a drilling instrument with the guide member to form a hole in the vertebra spaced from the endplate of the vertebra, the hole being in communication with the recess at an end thereof; and
    guiding the drilling instrument with the guide member to form a second hole in the second vertebra spaced from the endplate of the second vertebra, the second hole being in communication with the second recess at an end thereof.

2. The method of claim 1, further comprising:
    forming a hole in the vertebra in communication with the defect through the recess; and
    engaging the blocking member to the vertebra with an anchor extending through the blocking member and into the hole.

3. The method of claim 2, wherein forming the hole includes forming a circular hole.

4. The method of claim 2, wherein forming the hole includes forming a hole elongated transversely to the central axis of the spinal column.

5. The method of claim 1, wherein positioning the blocking member in the defect includes positioning the blocking member in the defect in a location recessed from an outer surface of the annulus.

6. The method of claim 1, further comprising forming a hole in the vertebra in communication with the recess.

7. The method of claim 6, wherein the hole is formed at an end of the recess remote from the defect.

8. The method of claim 6, further comprising:
    positioning an attachment portion of the blocking member in the hole; and
    positioning an anchor through the attachment portion and into the hole to engage the blocking member to the vertebra.

9. The method of claim 8, wherein the blocking member, attachment portion and anchor are recessed below an outer surface of the vertebra.

10. The method of claim 1, wherein the recess opens along an outer surface of the vertebra.

* * * * *